United States Patent
Dorsch

(10) Patent No.: US 8,191,406 B2
(45) Date of Patent: Jun. 5, 2012

(54) METHOD AND DEVICE FOR PRETREATING A FUEL ROD CLADDING TUBE FOR MATERIAL TESTS, TEST BODY AND METHOD FOR TESTING CORROSION CHARACTERISTICS

(75) Inventor: Thomas Dorsch, Erlangen (DE)

(73) Assignee: Areva NP GmbH, Erlangen (DE)

( * ) Notice: Subject to any disclaimer, the term of this patent is extended or adjusted under 35 U.S.C. 154(b) by 209 days.

(21) Appl. No.: 12/488,608

(22) Filed: Jun. 22, 2009

(65) Prior Publication Data

US 2009/0308144 A1 Dec. 17, 2009

Related U.S. Application Data

(63) Continuation of application No. PCT/EP2007/010419, filed on Nov. 30, 2007.

(30) Foreign Application Priority Data

Dec. 22, 2006 (DE) .......................... 10 2006 062 152

(51) Int. Cl.
*G01N 17/02* (2006.01)

(52) U.S. Cl. ............ 73/86; 376/261; 376/277; 376/305; 376/409; 376/414

(58) Field of Classification Search .................. 376/261, 376/277, 305, 409, 414; 73/86; 422/53
See application file for complete search history.

(56) References Cited

U.S. PATENT DOCUMENTS

| | | | |
|---|---|---|---|
| 3,556,870 A | | 1/1971 | Debray et al. |
| 3,850,701 A | * | 11/1974 | Itai et al. ...................... 428/472.2 |
| 3,909,370 A | | 9/1975 | Videm et al. |
| 4,425,193 A | | 1/1984 | Taylor |
| 5,024,733 A | * | 6/1991 | Abys et al. ..................... 205/257 |
| 5,260,218 A | | 11/1993 | Garde |
| 5,361,284 A | * | 11/1994 | Baum et al. .................... 376/245 |
| 5,889,401 A | | 3/1999 | Jourdain et al. |
| 5,991,352 A | | 11/1999 | Taylor |
| 6,369,566 B1 | | 4/2002 | McClelland |
| 2005/0234545 A1 | * | 10/2005 | Su et al. ........................ 623/1.46 |
| 2007/0201608 A1 | | 8/2007 | Model et al. |

FOREIGN PATENT DOCUMENTS

DE 2019663 A1 11/1971
(Continued)

OTHER PUBLICATIONS

Jourdain, et al—"Corrosion Performance of Optimised and Advanced Fuel Rod Cladding in PWRs at High Burnups", XP-001095337, pp. 153-160, Sweden, 1997.

(Continued)

*Primary Examiner* — Hezron E Williams
*Assistant Examiner* — Paul West
(74) *Attorney, Agent, or Firm* — Laurence A. Greenberg; Werner H. Stemer; Ralph E. Locher

(57) ABSTRACT

A method for treating or preparing a fuel rod cladding tube in such a way that an influence of iron oxide deposits on its surface can be studied and assessed precisely under virtually operational conditions with as little risk as possible, includes at least partially coating the fuel rod cladding tube with an iron oxide layer by immersing it in an aqueous electrolyte medium which contains iron oxide particles. The iron oxide particles are produced by anodic oxidation of an iron-containing working electrode. A test body and a device for pretreating a fuel rod cladding tube with an electrochemical three-electrode configuration, are also provided.

14 Claims, 1 Drawing Sheet

FOREIGN PATENT DOCUMENTS

| | | | |
|---|---|---|---|
| DE | 10 2006 009 502 B3 | 8/2007 |
| EP | 1089295 A1 | 4/2001 |
| GB | 2132345 A | 7/1984 |
| JP | 2-6783 A | 1/1990 |

OTHER PUBLICATIONS

International Search Report dated Mar. 26, 2008.

* cited by examiner

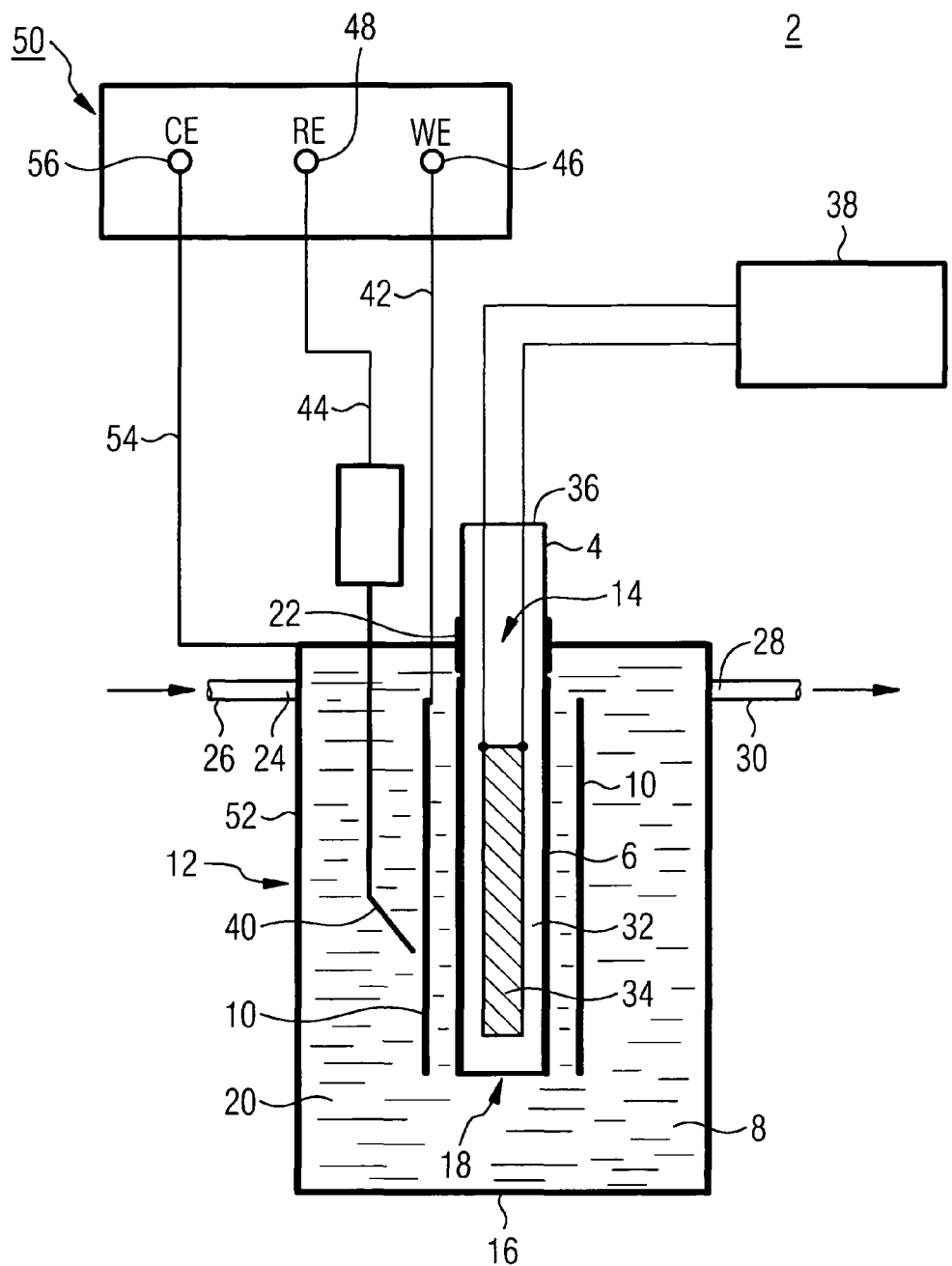

METHOD AND DEVICE FOR PRETREATING A FUEL ROD CLADDING TUBE FOR MATERIAL TESTS, TEST BODY AND METHOD FOR TESTING CORROSION CHARACTERISTICS

CROSS-REFERENCE TO RELATED APPLICATION

This is a continuation, under 35 U.S.C. §120, of copending International Application No. PCT/EP2007/010419, filed Nov. 30, 2007, which designated the United States; this application also claims the priority, under 35 U.S.C. §119, of German Patent Application DE 10 2006 062 152.2, filed Dec. 22, 2006; the prior applications are herewith incorporated by reference in their entirety.

BACKGROUND OF THE INVENTION

Field of the Invention

The invention relates to a method and a device for pretreating a fuel rod cladding tube for material tests, especially for testing corrosion behavior and in particular with an electrochemical three-electrode configuration. The invention furthermore relates to a fuel rod cladding tube used as a test body for a laboratory-based test of its corrosion characteristics and a method for testing corrosion characteristics.

The fuel assemblies of a nuclear reactor typically include a bundle of fuel rods. Each of the fuel rods has a fuel rod cladding, also referred to as a fuel rod cladding tube or cladding tube for short, which forms an external enclosure or envelope and contains inside it enriched nuclear fuel, for example in the form of sintered uranium dioxide pellets. The fuel rod cladding is intended to separate the nuclear fuel from the coolant which flows around the fuel assemblies or the fuel rods and to prevent fission products which are produced during nuclear fission from entering the coolant or making direct contact therewith.

In water-moderated nuclear reactors, the fuel rod cladding tubes are typically made from zirconium or from a zirconium alloy. Particularly, so-called ZIRCALOYS are used in this context, which, in addition to zirconium as the main component, can also contain minor amounts of tin, iron, nickel, chromium or niobium. Zirconium is a preferred material in the production of fuel rod claddings primarily due to its comparably low absorption cross sections for neutrons, or in other words due to its high neutron permeability, but also due to its high temperature resistance and good thermal conductivity.

Since, during operation of a nuclear reactor, the fuel rods are continuously exposed to the surrounding cooling medium which can contain a not inconsiderable fraction of oxidizing components or dissolved gases, for example oxygen, depending on the chemical conditioning and "reactor operational mode", an increase in corrosion of the ZIRCALOY surfaces is inevitable over the course of time. As a result, it is possible that the structural characteristics of the cladding tube material may change in an undesired manner which is disadvantageous in terms of operational safety. Corrosion is therefore one of the processes which limit the duration of use of the fuel assemblies in the reactor to about three to five years.

In addition to the formation of zirconium oxide layers, which is desired per se and contributes to the passivation of the ZIRCALOY surfaces of the cladding tubes, it is possible for so-called CRUD layers or deposits on the cladding tubes to form as a result of iron oxide particles which are dissolved or contained in the reactor cooling water, in particular during power operation of boiling-water reactors. CRUD (originally an acronym for "Chalk River Unidentified Deposit") is a term typically used by a person skilled in the art in this context to refer to a mixture or agglomeration of various iron oxides, in which foreign ions such as $Zn^{2+}$, $Mn^{2+}$, $Zr^{3+}$ or $Ni^{2+}$ can be included. In this case, the exact structure and composition of the oxides depends very strongly on the conditions prevailing during their formation, for example on the pH of the cooling water, on the temperature, on the presence of any foreign ions, etc.

Although there is a general consensus that such deposits usually have a rather disadvantageous effect on the integrity and durability of the underlying material, there has been little detailed research to date on the mechanisms of action, and so far it has not been possible to make comprehensive quantitative statements relating to the effects of CRUD layers on the corrosion behavior and the life span of fuel rod cladding tubes under the operational conditions which are customary in boiling-water reactors. That is in particular due to the fact that an in situ test of the CRUD deposit processes during the actual reactor operation is hardly practicable and even a thorough subsequent test of the fuel rod cladding tubes of "spent" fuel assemblies removed from the reactor pool are subject to considerable limitations due to the comparably high radiation load and is hardly possible in practice.

It would be desirable to attain well-founded insights and empirical data relating to the material characteristics and the corrosion behavior of possible cladding tube materials under the operational conditions to be expected even before a fuel assembly or a fuel rod cladding tube is used in the nuclear reactor in accordance with specifications, with the influence of iron oxide layers on the material surfaces which form in the course of subsequent reactor operation being deserving of particular consideration.

SUMMARY OF THE INVENTION

It is accordingly an object of the invention to provide a method and a device for pretreating a fuel rod cladding tube for material tests, a test body and a method for testing corrosion characteristics, which overcome the hereinafore-mentioned disadvantages of the heretofore-known methods and devices of this general type and which can be used to treat or prepare a fuel rod cladding tube in such a manner that the influence of iron oxide deposits on its surface can be studied and assessed precisely under virtually operational conditions with as little risk as possible.

With the foregoing and other objects in view there is provided, in accordance with the invention, a method for pretreating a fuel rod cladding tube for material tests, in particular for testing corrosion behavior. The method comprises providing an aqueous electrolyte medium, placing an iron-containing working electrode in the electrolyte medium, producing iron oxide particles in the electrolyte medium by anodic oxidation of the iron-containing working electrode, and at least partially coating the fuel rod cladding tube with an iron oxide layer by immersing the fuel rod cladding tube in the electrolyte medium containing the iron oxide particles.

In this context, the invention proceeds from the consideration that, for reasons of protection from radiation and operational reliability, systemic research on the influence of iron oxide layers on fuel rod cladding tubes on their stability and chemical integrity should expediently not be carried out in situ during real reactor operation, but within the framework of a simulation using a test object which is "fresh from the factory" and has not yet been contaminated by contact with radioactive nuclear fuel. Such a procedure furthermore appears appropriate since primarily electrochemical processes and characteristics are investigated which are influenced only comparatively weakly by the presence/absence of radioactive radiation. On the other hand, a fuel rod cladding tube fresh from the factory generally does not yet have a high-temperature oxide layer—and if it does, it is at most a zirconium oxide layer rather than the iron oxide-containing CRUD deposits which are of specific interest in this case. Therefore, the fuel rod cladding tubes must first undergo corresponding preparation, that is to say the CRUD layer must be applied in an "artificial" fashion.

It is conceivable for this purpose in principle to immerse the fuel rod cladding tube to be tested in a freshly prepared aqueous solution of iron salts, such as Fe(III) chloride, Fe(II) sulphate, FeOOH etc. or to inject such a solution into an autoclave containing the fuel rod cladding tube with the aid of a high-pressure injection pump, with the result that the iron oxides which are formed as a result of precipitation in the solution deposit on the cladding tube surface. It has been found, however, that, compared to the CRUD layers which form during real reactor operation, iron oxides which are produced in this way by precipitation always contain noteworthy fractions of included or bound anions, such as chloride or sulphate ions, which are released in subsequent series of tests and have a negative or falsifying effect on the (simulated) cooling water chemistry. As a result, such laboratory tests on correspondingly prepared ZIRCALOY cladding tubes under certain circumstances do not provide any reliable information relating to the characteristics and effects of the CRUD deposits which actually form during reactor operation.

Therefore, alternative preparation methods should be used, which avoid the contamination of the formed iron oxides with disturbing anions and result in deposits on the ZIRCALOY cladding tubes, which can be compared, in terms of their structure and composition, to the CRUD deposits formed as a result of operation. It has surprisingly been found that these requirements are met to a particular extent by an electrochemical method in which the production and deposition of iron oxides on a ZIRCALOY cladding tube take place under anodic oxidation of an iron-containing working electrode, such as a steel electrode, in an aqueous electrolyte medium.

In order to provide a particularly precise controllable and reproducible coating operation, the working electrode in this case is advantageously a constituent part of an electrochemical three-electrode configuration known to a person skilled in the art from the field of galvanization, in which the working electrode is held at a constant electric potential with respect to a reference electrode with the aid of an electronic control loop, referred to as potentiostat, by way of suitably controlling the current flowing through the electrolyte solution between the working electrode and an auxiliary electrode (counter electrode). Alternatively, a so-called galvanostatic circuit in the configuration is also possible, in which the current is kept at a constant prespecified value.

As opposed to the conventional galvanic coating in which, with reduction, the metal ions which enter into solution at the working electrode (load electrode) precipitate directly on the workpiece to be coated in the form of a metallic coating, that is to say the workpiece itself represents the electrode which is complementary to the working electrode, the concept which is present in this case provides that the fuel rod cladding tube is electrically insulated with respect to the electrodes of the three-electrode configuration or is only in material connection with them through the electrolyte solution. The iron ions which are liberated at the working electrode react at least partially with the molecules or ions of the aqueous electrolyte solution and in the process form, depending on the prevailing electric, water-chemical or other boundary conditions, various iron oxide particles or clusters thereof which are at first present in colloidal solution finely distributed in the liquid and gradually precipitate on the surface of the fuel rod cladding tube immersing therein, with the result that the desired CRUD-like deposits or coatings are produced there, which are free from anionic contaminations.

In accordance with another feature of the invention, it is particularly preferred if the growth of the iron oxide layer takes place under ambient conditions which are equal, in particular with respect to temperature and aggregate state of the medium surrounding the fuel rod cladding tube, to the in situ conditions in a boiling-water reactor during power operation. Therefore, the electrolyte solution is advantageously heated during the electrochemical pre-treatment of the fuel rod cladding tube in such a way that it is in the boiling state during the deposition of the iron oxide particles on the fuel rod cladding tube—at least in a spatial region which includes the immediate area surrounding the fuel rod cladding tube.

In accordance with a further feature of the invention, an electric heating device, which is preferably disposed in the tube interior of the fuel rod cladding tube, is dimensioned so as to be suitable with respect to its heating power and is used to heat the tube from the inside. Analogously with respect to the conditions during the reactor operation, in which the decay heat of the nuclear fuel which is enclosed by the fuel rod cladding tube ensures heating of the cladding tube wall, a thermal flow which is directed from the inside outward, that is to say a heat transfer from the fuel rod cladding tube to the surrounding cooling medium—in this case the electrolyte liquid—which may have been externally pre-adjusted to a specific temperature, is thus established in such a way that the cooling medium is brought into the boiling state or kept in it. Just as in a boiling-water reactor, the range of subcritical boiling (so-called nucleate boiling) is preferably established in this case, in which, in contrast to so-called film boiling, an intensive heat exchange with the cladding tube wall with a comparatively high heat transfer coefficient is ensured. The real operating conditions in a boiling-water reactor are thus imitated or simulated particularly well, with the result that the iron oxide layers which deposit on the fuel rod cladding tube are, in structural terms, practically identical to the CRUD layers which are formed due to operation in the reactor.

As already explained, the exact chemical composition of the iron oxide layers, in particular the ratio of iron(II, III) oxides ($Fe_3O_4$, so-called magnetite) to iron(III) oxides ($Fe_2O_3$, so-called hematite), depends on various details and boundary conditions of the electrochemical process control, but in particular on the "water chemistry" of the electrolyte solution. Therefore, in accordance with an added feature of the invention, the chemical composition of the iron oxide layer formed during deposition of the iron oxide particles on the fuel rod cladding tube, in particular the ratio of magnetite fractions to hematite fractions, is advantageously controlled by the introduction of gases, in particular of oxygen, into the electrolyte medium. In addition, liquid or solid additives with oxidizing or reducing effect can of course also be added to the aqueous electrolyte medium in order to control the ambient conditions during the deposition and thus the composition of the iron oxides.

It can moreover be appropriate, within the framework of systemic series of tests, to also study the influence of various foreign ions, as are present in the CRUD layers which are formed during reactor operation, in laboratory tests. Therefore, in accordance with an additional feature of the invention, the electrode material of the working electrode in the electrolytic preparation of the cladding tube is advantageously selected in such a way that the iron oxide layer which deposits on the tube surface contains a prespecified fraction of included foreign ions, preferably foreign metallic ions, in particular $Zn^{2+}$, $Mn^{2+}$, $Ni^{2+}$ and/or $Cr^{3+}$. That means that the electrode material expediently includes a correspondingly iron-based metal alloy.

The advantages attained by virtue of the invention are, in particular, to be found in the possibility of coating new fuel rod cladding tubes in a targeted manner, with the aid of an electrochemical method, especially with a suitable selection of the thermal and chemical ambient conditions, with iron oxide layers which are practically identical in terms of their structure and composition to those layers which are formed during the use of such cladding tubes in a boiling-water reactor. In particular, contamination of the iron oxide layers by included anions in this case are avoided, which would be impossible to avoid in the case of coating with the aid of an iron oxide-containing coating solution produced by dissolving iron salts. The use of high pressure injection pumps and the like which are susceptible to faults is likewise not necessary. Instead, composition, structure and formation rate of the iron oxides can be controlled precisely and in a targeted fashion using simple principles, such as Faraday's law, by varying influence parameters which are simple to manipulate.

Through the use of the fuel rod cladding tubes which are thus prepared and are subsequently used as a test body for a laboratory-based test of their corrosion behavior under the influence of the CRUD layers, systemic series of tests with respect to the necessary safety precautions and official guidelines, etc. are carried out in a significantly simplified manner. By varying the test parameters it is therefore comparatively simple and poses no risk to the surrounding area or to the operating personnel responsible for the test facility to be able to "play out" a series of scenarios, which would, for reasons of the official conditions alone, be practically impossible during real reactor operation. The findings gained in this case can then be taken into account in an appropriate fashion during design, conception, planning and implementation of the cladding tubes per se and, if appropriate, of further reactor components and in the selection of associated operating parameters, etc. Fuel assemblies can therefore be developed and qualified under conditions which are closer to reality than have been possible to date.

With the objects of the invention in view, there is also provided a method for pretreating a fuel rod cladding tube. The method comprises providing an electrochemical three-electrode configuration having an iron-containing working electrode in an aqueous electrolyte medium, regulating the three-electrode configuration on a current and/or voltage side with an associated potentiostat, and pretreating the fuel rod cladding tube in the aqueous electrolyte medium for a subsequent test of its corrosion characteristics.

With the objects of the invention in view, there is concomitantly provided a device for pretreating a fuel rod cladding tube for a subsequent test of its corrosion characteristics. The device comprises an aqueous electrolyte medium, an electrochemical three-electrode configuration including an iron-containing working electrode in the aqueous electrolyte medium, and a potentiostat for regulating the electrochemical three-electrode configuration on the current and/or voltage side.

Other features which are considered as characteristic for the invention are set forth in the appended claims.

Although the invention is illustrated and described herein as embodied in a method and a device for pretreating a fuel rod cladding tube for material tests, a test body and a method for testing corrosion characteristics, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The FIGURE of the drawing is a diagrammatic, longitudinal-sectional view of an exemplary embodiment of a configuration for coating a fuel rod cladding tube with an iron oxide layer, according to the invention.

DETAILED DESCRIPTION OF THE INVENTION

Referring now in detail to the single FIGURE of the drawing, there is seen a diagrammatically illustrated coating apparatus 2 which serves for coating a fuel rod cladding tube 4 that is composed of ZIRCALOY, for a fuel rod in a boiling-water reactor with an iron oxide layer 6. The aim is to apply a layer onto the outer surface of the fuel rod cladding tube 4. The layer includes iron oxide particles so that, in terms of its chemical composition, its microscopic structure and its other physical and chemical characteristics, it corresponds as much as possible to the iron oxide layer which is also referred to as CRUD and which forms during the intended use of such a cladding tube 4 in a boiling-water reactor. For this purpose, the operating mode of the coating apparatus 2 is based on a basic electrochemical principle according to which the fuel rod cladding tube 4 is coated with the desired iron oxide layer 6 by immersing it in an aqueous electrolyte medium 8 which contains iron oxide particles. The iron oxide particles are produced by way of anodic oxidation of an iron-containing working electrode 10, in this case a steel electrode with low fractions of metallic foreign ions, and are provided in the electrolyte medium 8.

To this end, the coating apparatus 2 specifically includes a metallic pressure vessel 12 which is also referred to as an autoclave, is thermally isolated from the outside and can be closed in a pressure-tight manner. The pressure vessel 12 has a through opening 14 in a vessel wall 16, through which the fuel rod cladding tube 4 to be coated can be inserted into a vessel interior 20 from the outside with its lower closed end 18. An annular and electrically isolating sealing element 22, for example made of TEFLON, is disposed between the outside of the fuel rod cladding tube 4 and the inner surface of the through opening 14. Due to the sealing element 22, firstly the seal-tightness of the configuration when the fuel rod cladding tube 4 is inserted is ensured, and secondly the fuel rod cladding tube 4 is electrically isolated from the metallic vessel wall 16.

The aqueous electrolyte medium 8 is fed to the vessel interior 20 of the pressure vessel 12 by way of a feed line 26 which is connected to an inlet connection 24. If necessary, "used" electrolyte medium 8 can be removed again or discharged by way of a removal line 30 which is connected to an outlet connection 28. To this end, corresponding control valves, which can also be used to regulate the pressure of the vessel interior and are not illustrated herein, are integrated in the feed line 26 and in the removal line 30.

In the present case, a continuous throughput of electrolyte solution 8 through the pressure vessel 12 and thus a constant flow around the fuel rod cladding tube 4 which is immersed into the electrolyte solution 8 during the coating operation is provided, to which end the "used" proportion which has been removed through the removal line 30 is chemically conditioned or "freshened" in a non-illustrated conditioning apparatus, if necessary with the addition of chemically active additives, degassed or enriched with gases, and subsequently fed back into the pressure vessel 12 again through the feed line 26 with the aid of a delivery pump in the manner of a circular liquid flow. The non-illustrated delivery pump can be present in the form of a compression pump in order to pressurize the electrolyte medium 8 in the vessel interior 20 in accordance with a set compression power.

Furthermore, a non-illustrated heating device which is connected into the feed line 26 can be used to (pre-) adjust the temperature of the medium flowing into the pressure vessel 12, with the result that overall the pressure and temperature conditions of the high-temperature cooling water flowing into the reactor pressure vessel in a boiling-water reactor are imitated or simulated.

The boiling-water reactor conditions can be reproduced even more closely by heating the fuel rod cladding tube 4 during the electrochemical coating from the inside, as a result of which a heat transfer from a cladding tube wall 32 to the surrounding cooling medium, which takes place during the reactor operation and in this case is caused by the radioactive decay process of the nuclear fuel, is simulated. For this purpose, an electric heating device 34, for example a cylindrical high-power heating cartridge, can be inserted into the fuel rod cladding tube 4 from an upper, unclosed end 36 projecting from the pressure vessel 12. The electric heating device 34 is disposed in a cavity which is enclosed by the cladding tube wall 32 of the fuel rod cladding tube 4. In order to avoid unwanted potential shifts in the cladding tube wall 32, heating coils of the heating device 34 are galvanically isolated from an external power supply. An associated regulation device 38 regulates the heating current and thus the heating power in such a way that the electrolyte medium 8, at least in the immediate vicinity of the cladding tube section which projects into the pressure vessel 12, is brought into the boiling state and is maintained there during the electrochemical coating process. The formation of large-area boiling films on the cladding tube surface, which can negatively affect the heat transfer, should be avoided in this case by way of appropriate regulation of the heating power.

The iron oxide particles necessary for coating the fuel rod cladding tube 4 are produced by the anodic oxidation of the iron-containing working electrode 10, in which iron ions detach from the electrode surface and react with the aqueous components of the electrolyte solution 8 to form various iron oxides which, after primarily convective transport through the pressure vessel 12, eventually precipitate as desired on the surface of the fuel rod cladding tube 4.

The working electrode 10 is configured in the manner of a hollow cylinder and is disposed at a spacing of a few centimeters or less concentrically around the fuel rod cladding tube 4, in order to provide as uniform and homogenous a coating of the fuel rod cladding tube 4 as possible. A reference electrode 40, which is associated therewith on the potential side, is immersed in the electrolyte medium 8, outside the hollow cylinder formed by the working electrode 10. The working electrode 10 and the reference electrode 40 are each connected over a respective connection line 42, 44, which is led through the vessel wall 16 of the pressure vessel 12 in an electrically isolated manner, to a respective input 46, 48 of a high-voltage potentiostat 50. The potentiostat 50 is provided for voltage regulation purposes and operates on the principle of a differential operational amplifier. A third electrode necessary for a potential-regulated three-electrode configuration, a so-called counter electrode 52 or auxiliary electrode, is formed by the vessel wall 16 of the pressure vessel 12 itself in the exemplary embodiment. In an alternative embodiment, however, a separate counter electrode including, for example, platinum can also be provided in the vessel interior 20 of the pressure vessel 12, in particular in the form of a spiral which winds around the working electrode 10 and the reference electrode 40. The counter electrode 52 is connected to an output 56 of the operational amplifier of the potentiostat 50 by way of a connection line 54.

The potentiostat 50 measures in principle the voltage between the reference electrode 40 and the working electrode 10 at a very high-resistance input, compares the voltage to a set predetermined value and correspondingly adjusts a current by way of the counter electrode 52 in such a way that the difference between actual value and predetermined value of the potential disappears. The control loop is closed by the electrochemical cell with the electrolyte 8 itself and the current flows through the working electrode 10 back to ground. In this manner, even in the case of process-related fluctuations in the current intensity by several decades, it is possible to control the electric potentials with pronounced precision and good reproducibility.

The other chemical and physical process parameters relevant for the iron oxide production and coating of the fuel rod cladding tube 4, such as the oxygen content dissolved in the electrolyte circuit or the temperature at the cladding tube surface, can also be influenced, controlled and recorded in a simple and targeted fashion. By avoiding interfering anionic included substances and due to the boundary and ambient conditions which correspond to the conditions in a boiling-water reactor, it is thus possible to produce, in a comparatively simple manner, contamination-free iron oxide layers 6 on ZIRCALOY cladding tubes 4, in which the iron oxide layers are comparable in terms of structure and composition to real CRUD. The success of the method can be evidenced by various qualitative and quantitative verification methods, for example by X-ray diffractometry.

The invention claimed is:

1. A method for pretreating a fuel rod cladding tube for material tests, the method comprising:
   providing an aqueous electrolyte medium;
   providing an electrochemical three-electrode configuration having an iron-containing working electrode as one of said three electrodes;
   providing a fuel rod cladding tube;
   placing said fuel rod cladding tube in said medium;
   placing said three-electrode configuration having said iron-containing working electrode in the electrolyte medium;
   producing iron oxide particles in the electrolyte medium by anodic oxidation of the iron-containing working electrode; and
   at least partially coating the fuel rod cladding tube with an iron oxide layer by immersing the fuel rod cladding tube in the electrolyte medium containing the iron oxide particles said coating being free from anionic contaminations.

2. The method according to claim 1, which further comprises testing corrosion behavior of the pretreated fuel rod cladding tube.

3. The method according to claim 1, which further comprises heating the electrolyte medium to maintain a boiling state during deposition of the iron oxide particles on the fuel rod cladding tube.

4. The method according to claim 1, which further comprises heating the electrolyte medium to maintain a subcritical boiling state during deposition of the iron oxide particles on the fuel rod cladding tube.

5. The method according to claim 1, which further comprises heating the fuel rod cladding tube with a heating device disposed in an interior of the fuel rod cladding tube.

6. The method according to claim 1, which further comprises controlling a chemical composition of the iron oxide layer formed during deposition of the iron oxide particles on the fuel rod cladding tube by introducing gases into the electrolyte medium.

7. The method according to claim 6, which further comprises carrying out the controlling step by controlling a ratio of magnetite fractions to hematite fractions.

8. The method according to claim 6, which further comprises carrying out the step of introducing gases by introducing oxygen.

9. The method according to claim 1, which further comprises selecting an electrode material of the working electrode to cause the iron oxide layer being deposited on the fuel rod cladding tube to contain a fraction of included foreign ions.

10. The method according to claim 9, wherein the foreign ions are foreign metallic ions.

11. The method according to claim 10, wherein the foreign metallic ions include foreign metallic ions selected from at least one of the group consisting of $Zn^{2+}$, $Mn^{2+}$, $Ni^{2+}$ and $Cr^{3+}$.

12. A test body for a laboratory-based test of corrosion characteristics, the test body comprising:
a fuel rod cladding tube pretreated according to claim 1.

13. A method for performing a laboratory-based test of corrosion characteristics, the method comprising the following steps:
testing the corrosion characteristics with a test body formed of a fuel rod cladding tube pretreated according to claim 1.

14. A method for pretreating a fuel rod cladding tube, the method comprising the following steps:
providing an electrochemical three-electrode configuration having an iron-containing working electrode as one of said three electrodes in an aqueous electrolyte medium;
regulating the three-electrode configuration on at least one of a current or voltage side with an associated potentiostat; and
pretreating the fuel rod cladding tube in the aqueous electrolyte medium for a subsequent test of its corrosion characteristics by at least partially disposing an iron oxide layer on said fuel rod that is free from anionic contaminations.

* * * * *